United States Patent
Cai et al.

(10) Patent No.: US 12,298,292 B1
(45) Date of Patent: May 13, 2025

(54) STUDY METHOD FOR CHLORITE GROWTH PATTERN BASED ON IN-SITU HIGH-PRECISION OBSERVATION MEANS

(71) Applicant: Chengdu University of Technology, Chengdu (CN)

(72) Inventors: Laixing Cai, Chengdu (CN); Weixue Guo, Chengdu (CN); Chengfang Yuan, Chengdu (CN); Tian Yang, Chengdu (CN); Yaohui Dong, Chengdu (CN); Yuhang Li, Chengdu (CN)

(73) Assignee: Chengdu University of Technology, Chengdu (CN)

( * ) Notice: Subject to any disclaimer, the term of this patent is extended or adjusted under 35 U.S.C. 154(b) by 0 days.

(21) Appl. No.: 18/989,220

(22) Filed: Dec. 20, 2024

(30) Foreign Application Priority Data

Mar. 13, 2024 (CN) .......................... 202410284332.0

(51) Int. Cl.
*G01N 33/44* (2006.01)
*G01N 23/2251* (2018.01)
(Continued)

(52) U.S. Cl.
CPC ......... *G01N 33/24* (2013.01); *G01N 23/2251* (2013.01); *G06F 30/28* (2020.01); *G06F 2111/10* (2020.01); *G06F 2113/08* (2020.01)

(58) Field of Classification Search
CPC .... G01N 33/24; G01N 23/2251; G06F 30/28; G06F 2111/10
See application file for complete search history.

(56) References Cited

U.S. PATENT DOCUMENTS

| 9,874,551 B2 * | 1/2018 | Herron ................... G01N 33/24 |
| 11,568,111 B2 * | 1/2023 | Zhou ....................... G06F 30/25 |

(Continued)

FOREIGN PATENT DOCUMENTS

| CN | 105784965 A | 7/2016 |
| CN | 112858131 B | 5/2021 |

(Continued)

OTHER PUBLICATIONS

Xiaodong Cui, "Study on the classification of chlorite rock mass quality on the fracture surface of dam foundation" Yunnan Water Power , 01, Feb. 15, 2008 (Feb. 15, 2008), full text.

(Continued)

*Primary Examiner* — Ricky Go
(74) *Attorney, Agent, or Firm* — Birchwood IP

(57) ABSTRACT

The present invention belongs to the technical field of petroleum and natural gas exploration and development, and specifically relates to a study method for chlorite growth pattern based on an in-situ high-precision observation means. The method includes: S1: selecting a sample and quantitatively characterizing mineral components; S11: selecting a typical sandstone sample developed with a chlorite coating and cement, grinding a rock slice, and observing under a microscope and a scanning electron microscope to determine a basic morphological characteristic, occurrence state and type of the chlorite; S2: performing data preprocessing on the sample; S3: establishing a water-rock numerical simulation model; S4: developing a water-rock numerical simulation experiment; S5: analyzing a water-rock numerical simulation result; and S6: explaining and applying the water-rock numerical simulation result.

2 Claims, 8 Drawing Sheets

(51) Int. Cl.
  *G01N 33/24* (2006.01)
  *G06F 30/28* (2020.01)
  *G06F 111/10* (2020.01)
  *G06F 113/08* (2020.01)

(56) References Cited

U.S. PATENT DOCUMENTS

2019/0257810 A1\* 8/2019 Lander .................. G01N 33/24
2024/0053322 A1\* 2/2024 Ma .................... G06F 18/24317

FOREIGN PATENT DOCUMENTS

| CN | 115128247 B | 9/2022 |
| CN | 117669207 A | 3/2024 |

OTHER PUBLICATIONS

Wang Wenyuan, Gao Jian, Wang Kun, Li Kaide, "Study on the Use of Fr actur e Chlor itization Rock Mass in the Dam Foundation of J in' anqiao Hydropower Station", Water Power vol. 32. No. 11, Nov. 21, 2006 (Nov. 21, 2006), full text.

\* cited by examiner

Well 5-1941.09 m Single polarization

STUDY METHOD FOR CHLORITE GROWTH PATTERN BASED ON IN-SITU HIGH-PRECISION OBSERVATION MEANS

CROSS-REFERENCE TO RELATED APPLICATIONS

This application claims priority to Chinese Patent Application No. 202410284332.0, filed on Mar. 13, 2024, which is hereby incorporated by reference in its entirety.

TECHNICAL FIELD

The present invention belongs to the technical field of petroleum and natural gas exploration and development, and specifically relates to a study method for chlorite growth pattern based on an in-situ high-precision observation means.

BACKGROUND

A chlorite mineral widely distributed in the earth surface system is one of the most important gap fillers in sandstone and has outstanding characteristics such as fine crystals, rich types, variable occurrence, and complex genesis. The formation of the chlorite mineral involves the entire geological process of structure, sedimentation and diagenesis, and records information on water-rock-hydrocarbon interactions across the entire basin at multiple scales. Meanwhile, the chlorite coating also plays a significant protective role on intergranular pores by offsetting compaction-pressure solution and inhibiting siliceous cementation, and can be regarded as a typical mineral for exploring high-quality reservoirs. Therefore, the analysis of the growth pattern of the chlorite mineral in sandstone is of great studying value for understanding the material migration process in oil and gas basins, and has important application value in the fields of reservoir geology, environmental geology, oil and gas exploration and material research and development.

An in-situ high-precision observation means can perform high-density and high-precision direct observation of the chlorite growth process by systematic sampling and an advanced chemical characteristic characterization technology of mineral rocks. For example, by using a high-resolution microscope such as a scanning electron microscope and an atomic force microscope, detailed observations of the morphological structure of a chlorite crystal can be achieved. Combined with an electron probe, energy spectrum analysis, and an X-ray diffractometer, the components and elemental compositions of the chlorite mineral are analyzed and summarized, which can classify the types of chlorite in actual sample and summarize genesis, thus helping to construct a growth model of chlorite under an actual geological condition. The water-rock numerical simulation technology is a method for achieving ordered evolution of physical and chemical characteristics of rock minerals by means of a powerful computer simulation and numerical calculation method and presenting a distribution pattern by colors and graphs. By establishing a proper geological model and a proper mathematical model and considering hydrogeological conditions and the lithology characteristics of the minerals, the growth, transformation and dissolution processes of the minerals can be simulated, and the distribution characteristics of the chlorite at different stages are finally obtained. This simulation method can simulate and explain the growth process of the chlorite by providing the dynamic change pattern in the growth process of the chlorite, and helps to deeply understand and predict the growth pattern of chlorite.

At present, the study on the chlorite growth pattern mainly includes a traditional geological method and a numerical simulation experiment. The traditional geological method mainly summarizes occurrence states and mineral characteristics in detail by using qualitative and semi-quantitative observation means; and the numerical simulation experiment mainly describes the formation, transformation and distribution of different minerals under various geological conditions by setting some water-rock interaction parameters (temperature, pressure, and time).

However, the traditional geological method aims at the characterization of current geological results and cannot accurately capture the dynamic evolution pattern in the chlorite growth process; and the numerical simulation is often too idealistic and lacks quantitative models of actual geological conditions, which makes it difficult for simulation results to match the actual geological environment in which the chlorite mineral grows. The application of these two methods alone leads to limited and inaccurate results. Therefore, an in-situ high-precision observation method needs to be effectively connected with the water-rock numerical simulation technology to accurately, finely and dynamically restore the growth process of the chlorite mineral in the sandstone.

SUMMARY

An objective of the present invention is to provide a study method for chlorite growth pattern based on an in-situ high-precision observation means, which can clarify the types and contents of mineral components, growth environment and distribution pattern of the chlorite mineral by performing fine observation on the chlorite mineral in a sandstone sample so as to obtain quantitative data of chlorite growth under actual geological conditions.

The present invention adopts the following specific technical solution.

A study method for chlorite growth pattern based on an in-situ high-precision observation means includes the following steps:

S1: Selecting a sample and quantitatively characterizing mineral components;

the S1 includes the following specific substeps:

S11: selecting a typical sandstone sample developed with a chlorite coating and cement, grinding a rock slice, and observing under a microscope and a scanning electron microscope to determine a basic morphological characteristic, occurrence state and type of the chlorite;

S12: performing a whole-rock clay mineral X-ray diffraction experiment on the same sandstone sample to obtain types and contents of related minerals contained in a chlorite growth environment;

S13: selecting a proper observation point to perform electron probe and energy spectrum analysis experiments on a chlorite developed with a typical grain coating, a pore lining and a pore filling in the sample based on a growth sequence from early to late to obtain element types and mineral component contents of different types of chlorites. The proper observation point refers to a point where the chlorite is well developed and easy to be subjected to the electron probe and energy spectrum analysis experiments.

S2: Performing data preprocessing on the sample;

the data preprocessing in the S2 is performed in the following manners:

preliminarily extracting environmental conditions required for the growth of the chlorite in different occurrences and growth stages from the observation data and experimental results, and wherein the environmental conditions required for the growth of the chlorite include salinity, pH value, temperature, and pressure; and preliminarily calculating types and contents of minerals required for the growth of the chlorite at different stages, reactive ions involved in the growth process, and a range of formation temperature and pressure parameters, so as to provide actual geological data support for water-rock numerical simulation.

S3: Establishing a water-rock numerical simulation model;

In the S3, based on the principle of a water-rock simulation experiment program and combined with results of geochemical test analysis, the chlorite growth environment in the actual sample is determined, the environmental conditions and fluid characteristic parameters required by the chlorite growth process are supplemented and improved, a simulation equation suitable for the chlorite sample is selected, and a chlorite water-rock interaction numerical model conforming to the geological condition of a study area is established.

S4: Developing a water-rock numerical simulation experiment;

in the S4, according to the experimental parameter data obtained in the S2-S3, chlorite reaction models of different types and different growth stages are established based on water-rock numerical simulation modeling and reaction principles, and water-rock numerical simulation is performed.

S5: Analyzing a water-rock numerical simulation result;

in the S5, the simulation result is obtained in the following manner:

intercepting experiment charts under different time, temperature and pressure conditions based on the simulation experiment process and the growth time sequence of the chlorite, and after performing analysis according to geological pattern to obtain growth models and distribution patterns of the chlorite at different development stages. The experiment charts refer to screenshots of the simulation experiment.

S6: Explaining and applying the water-rock numerical simulation result;

in the S6, based on the analysis of the simulation experiment result, the simulation result is used to provide a reasonable and scientific geological and numerical model for the chlorite growth process in the sandstone, and to explain, optimize and predict the chlorite growth pattern.

The present invention achieves the following technical effects:

The study method for chlorite growth pattern based on the in-situ high-precision observation means according to the present invention sets initial environmental parameters based on the in-situ high-precision observation means on the premise of fully considering the constraint of actual geological conditions, and simulates the chlorite growth process, development characteristics and distribution scale by the water-rock numerical simulation technology. This method focuses on solving key problems such as the lack of chlorite growth simulation experiments, unclear dynamic change characteristics during chlorite growth process, unclear chlorite growth patterns and influencing factors, and difficult to predict chlorite growth behaviors.

The study method for chlorite growth pattern based on the in-situ high-precision observation means according to the present invention clarifies the types and contents of mineral components, growth environment and distribution pattern of the chlorite mineral by performing fine observation on the chlorite mineral in a sandstone sample so as to obtain quantitative data of chlorite growth under actual geological conditions; and then performs forward modeling, interpretation and prediction through numerical simulation methods after constructing the geological model. This method provides a more accurate, more comprehensive and more effective means for studying the chlorite growth pattern, and has important scientific and application values.

wherein the solution flows from left to right; and

Figure 8:
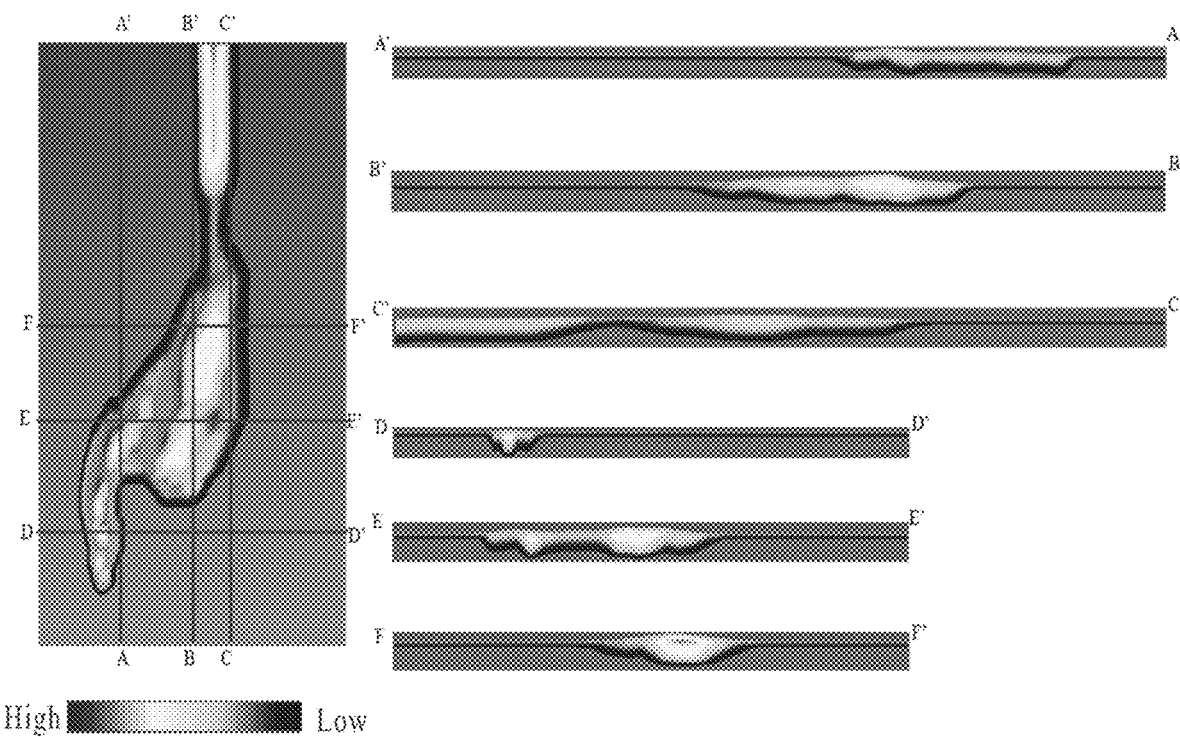

FIG. 8 shows a planar distribution characteristic of chlorite and a cross-sectional distribution morphology of different measurement lines according to an embodiment of the present invention.

DESCRIPTION OF EMBODIMENTS

To make the objectives and advantages of the present invention more apparent, the present invention is described in detail below with reference to the examples. It should be understood that the following description is only used to describe one or several specific embodiments of the present invention, and does not strictly limit the scope of protection specifically requested by the present invention.

The specific technical solution of the present invention is illustrated by taking a tight sandstone reservoir in a certain area of the Sichuan Basin as an example.

As shown in FIGS. 1 to 8, the study method for chlorite growth pattern based on the in-situ high-precision observation means includes the following steps:

S1: Selecting a Sample and Quantitatively Characterizing Mineral Components.

A proper observation point in a chlorite growth area is selected, and the morphology, occurrence structure and mineral components of a chlorite crystal are observed, recorded and analyzed using high-resolution microscopy, scanning electron microscope, electron probe, and energy spectrum analysis.

Figure 1:
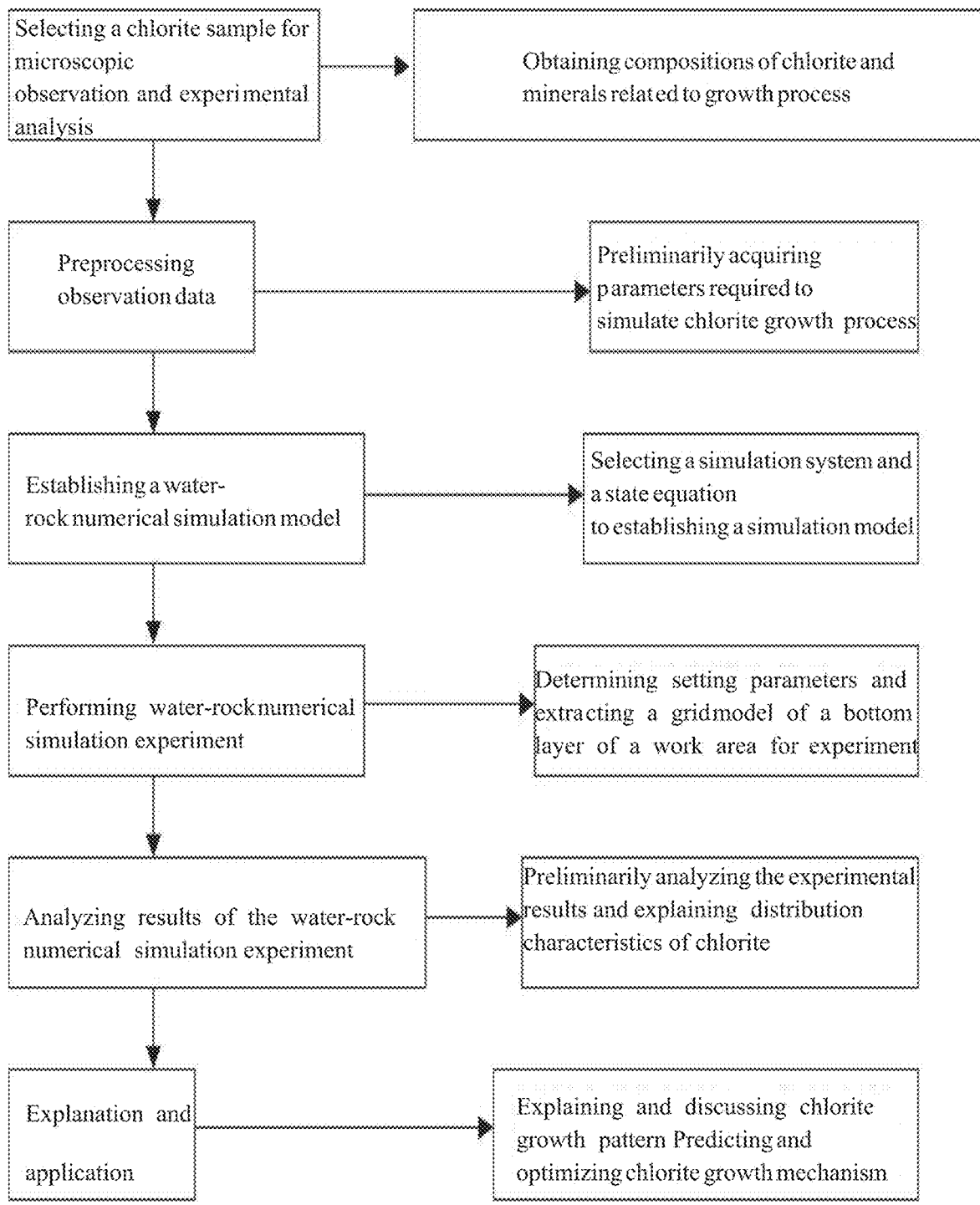
FIG. 1 is a flow chart of a study method for chlorite growth process according to an embodiment of the present invention.
Figure 2:
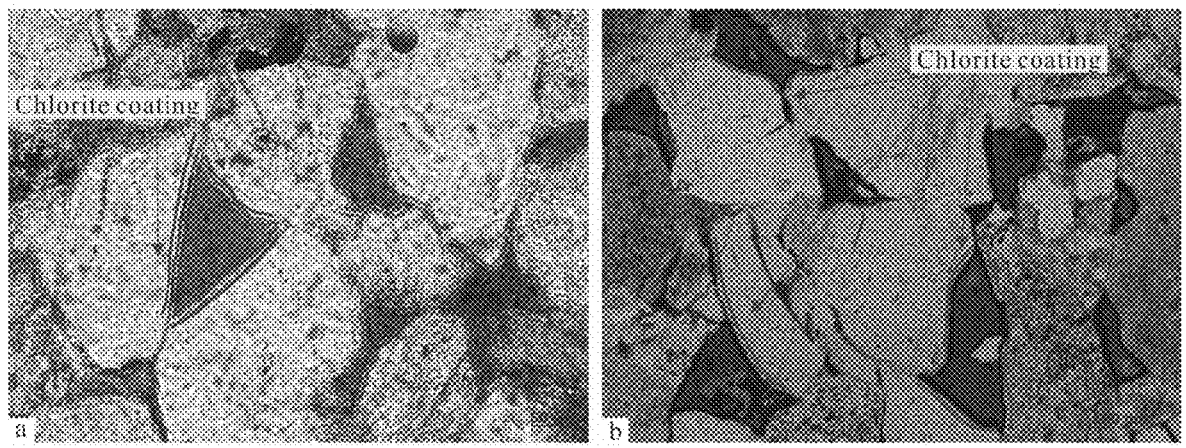
FIG. 2 is a diagram of a development characteristic of a chlorite coating in a certain area of the Sichuan Basin under a polarizing microscope according to an embodiment of the present invention.

1. A typical drilling rock core of the tight sandstone reservoir in the study area is selected and ground into a rock thin section, the rock thin section is observed under a Zeiss Axioscope A1 APOL. digital transmission and reflection polarizing microscope, and typical samples with developed chlorite are selected for use (wells 1-5 in the study area). The spare samples are observed by using a Zeiss Axioscope A1 APOL. digital polarizing microscope combined with scanning electron microscope to distinguish the development characteristics and genesis of chlorite: the chlorite can be classified into terrestrial chlorite and authigenic chlorite based on genesis. The terrestrial chlorite is mainly dispersed among the grains in the form of matrix, and the crystal morphology is irregular due to abrasion. The authigenic chlorite exists mainly in the form of cement in the pores between grains, is mostly produced in aggregates with a high degree of augerism, and can be further classified into chlorite-coated type and pore-filling type. The chlorite coating includes two forms: grain-coated chlorite and pore-lining chlorite. After a tight sandstone sample in a study area is ground into a common slice for observation by a microscope, the chlorite coating on the surface of the grains has significant characteristics, as shown in FIG. 2.

Figure 3:
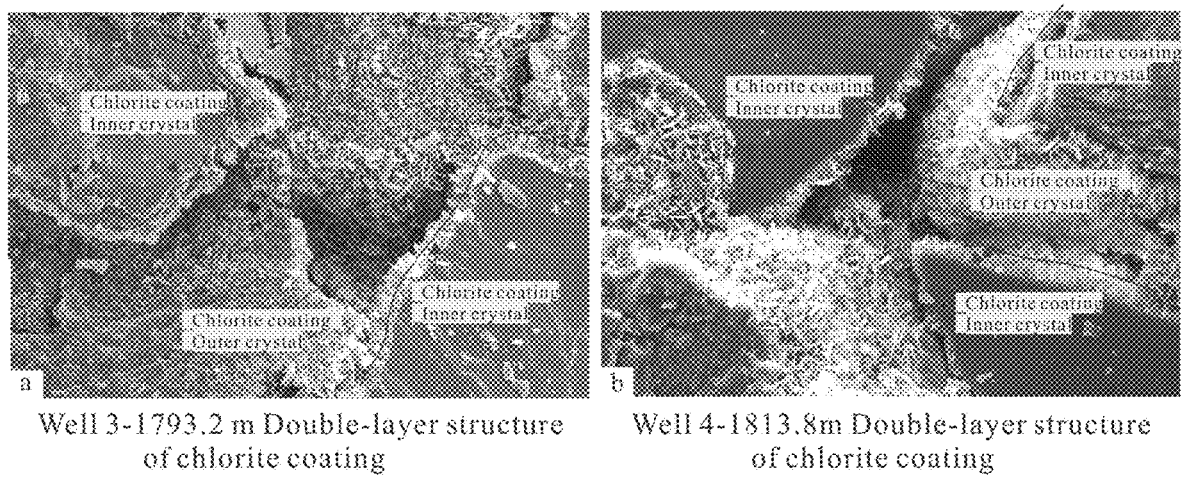
FIG. 3 is a diagram of a development characteristic of a chlorite coating in a certain area of the Sichuan Basin under a scanning electron microscope according to an embodiment of the present invention.
Figure 4:
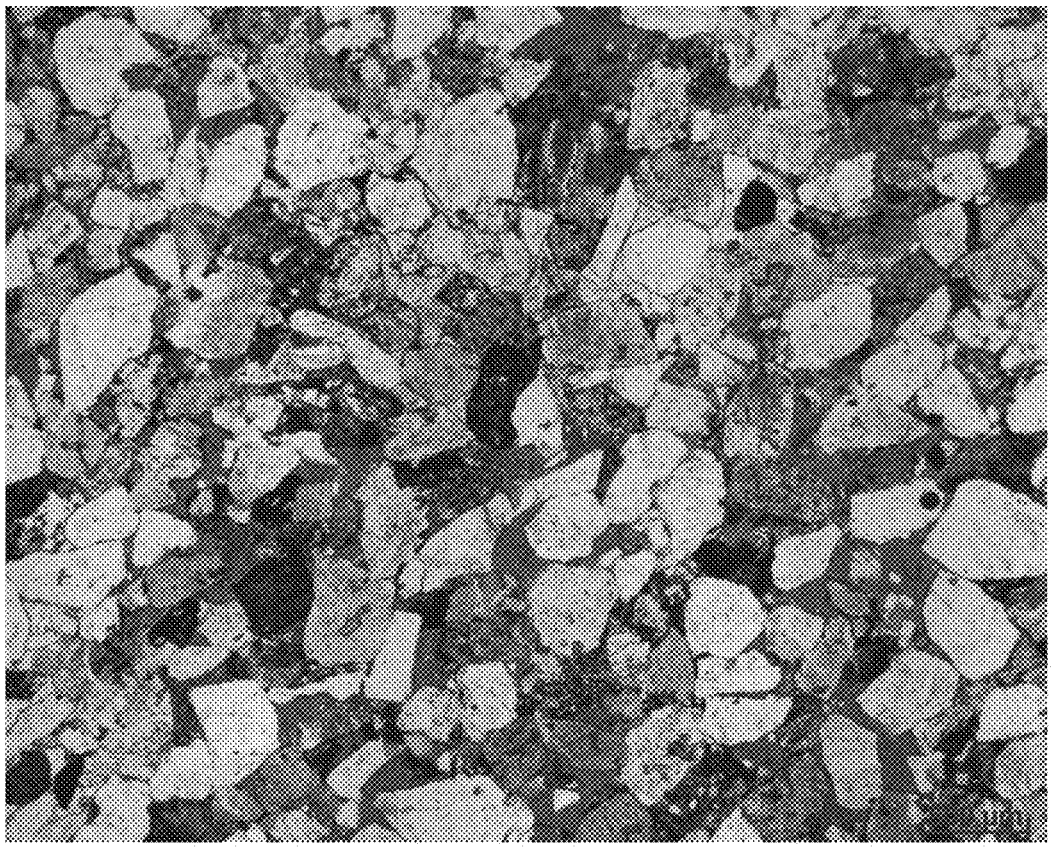
FIG. 4 shows a microscopic characteristic of a rock thin section of a lithic feldspathic sandstone in a certain area of Sichuan Basin according to an embodiment of the present invention.

The current study suggests that the chlorite coating has a double-layer structure, in which the inner layer of crystal close to the grain is relatively homogeneous and poorly euhedral; the outer layer of crystal close to the pore is mainly pore-lining chlorite, as shown in FIG. 3. By summarizing the previous study, it is known that the formation process of the iron-rich chlorite coating in the study area mainly includes three growth stages:

(1) Early precipitation of iron-rich clay coating: The chlorite coating in the study area is not developed at the contact point of the grains, and there is a lack of terrestrial iron-rich clay coating, which indicates that the authigenic iron-rich clay coating is the initial material of the inner layer of chlorite. The sedimentary water bodies in the study area during the syngenetic sedimentary period (early chlorite precipitation stage) are characterized by salinization, which is significantly different from that of freshwater rivers with terrestrial input. A large amount of iron flocs formed by chemical differentiation when the rivers enter the lake form a clay coating precipitated around the debris grains in the early stage after hydrolysis and recrystallization.

(2) Growth of an inner chlorite coating: The early clay coating can be corroded and recrystallized in a diagenesis period, and can be gradually transformed into an inner chlorite coating under the environment rich in $Fe^{3+}$ and $Mg^{2+}$;

(3) Growth of an outer chlorite coating: In the iron and magnesium ion-rich pore water, the pore lining chlorite attached to the inner chlorite coating and growing can be crystallized and precipitated. In addition to iron flocculation, the rich intermediate-basic igneous rock debris and ferromagnesian dark minerals provided by the source area can provide a certain degree of material basis for the formation of chlorite; in addition, the study area develops typical lacustrine sedimentary strata, which are mainly interlayers of sand and mud. Thick mudstone can inject pressure-released water containing $Fe^{3+}$ and $Mg^{2+}$ into the sandstone reservoir, which can also provide certain material conditions for the formation of chlorite.

2. Selecting a proper sample for experimental analysis. Firstly, a typical thin section is selected for systematic mineral component identification to preliminarily clarify the overall material composition of the chlorite-developed areas of the sandstone sample.

Figure 5:
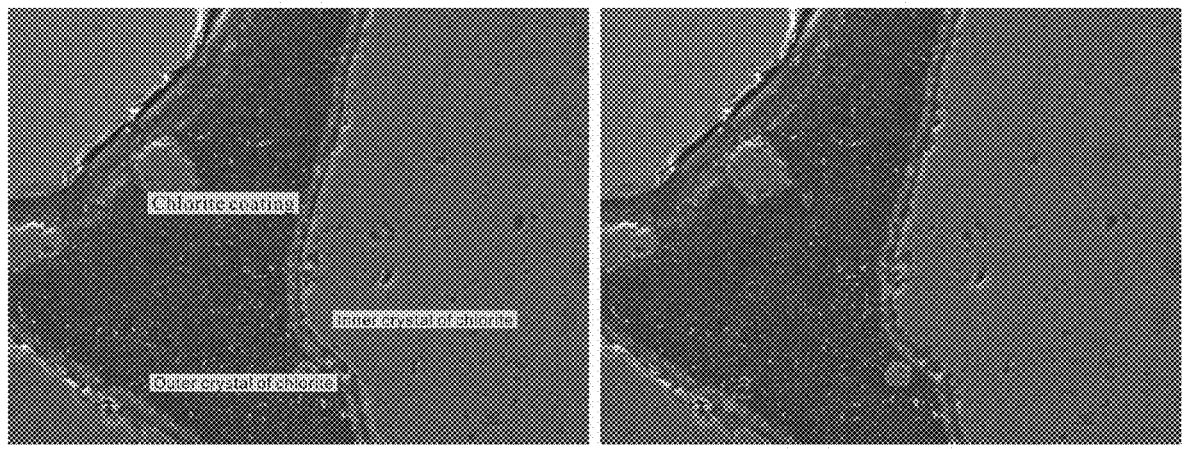
FIG. 5 is a schematic diagram of an electron probe dotting position of chlorite coating according to an embodiment of the present invention.

For example, sample 5 is selected for microscopic observation, as shown in FIG. 5, and a preliminary mineral component identification report is obtained (Table 1). To restore the growth environment and material composition of chlorite as much as possible, a chlorite-rich sandstone sample is selected for whole-rock X-diffraction analysis to obtain the mineral components present in the rock; the composition, type and content of clay minerals in the sample are obtained by further conducting clay mineral X-diffraction experiments; for the chlorite development site, electron probe and energy spectrum analysis are performed to obtain the mineral components and element ratios of chlorite. Based on the measured mineral component and content and clay mineral types, the initial mineral types and proportions in the chlorite growth environment are set; the elemental composition analysis results of chlorite are of great reference significance for selecting the specific types of initial minerals and the chemical ions involved in the chlorite growth process.

TABLE 1

Analysis and identification report of thin section of chlorite-containing sandstone sample.

| | Terrestrial debris | | | | | Non-terrestrial debris | Gap filler | | | | / |
|---|---|---|---|---|---|---|---|---|---|---|---|
| Depth | Quartz | Flint | Chlorite | Feldspar | Rock debris | Flaky mineral | Volcanic debris | Clay matrix | Silica | Calcite | Chlorite | Plane porosity |
| Content (%) | 50 | 1 | 1 | 11 | 15 | 1 | 1 | 1.5 | 0.5 | 1 | 2 | 15 |

The whole-rock clay experiment analysis is performed on the sample obtained from well 3, and the results are shown in Table 2:

TABLE 2

Whole-rock analysis results of rock sample at 4822.87 m from well 3

| No. | Quartz | Potassium feldspar | Plagioclase | Laumontite | Calcite | Total amount of clay |
|---|---|---|---|---|---|---|
| Sample from well 3 | 29.6 | 8.3 | 20.5 | 3.7 | 17.9 | 20.0 |

The clay mineral X-diffraction experiment is performed on the sample at the same depth, and the results are shown in Table 3:

TABLE 3

Relative content of clay minerals in the rock sample at 4822.87 m from well 3

| | Relative content of clay mineral (%) | | | | | | Illite/smectite mixed layer ratio | |
|---|---|---|---|---|---|---|---|---|
| No. | Kaolinite K | Chlorite C | Illite I | Smectite S | Illite/smectite mixed layer | Chlorite/smectite mixed layer | Smectite layer | Illite layer |
| Sampel from well 3 | 12 | 54 | 9 | / | 25 | 0 | 35 | 65 |

The chlorite mineral in the same sample is dotted for electron probe analysis (FIG. 5), and the results are shown in Table 4:

TABLE 4

Electron probe analysis results of rock sample at 4822.87 m from well 3

| No. | $Na_2O$ | MgO | $Al_2O_3$ | $SiO_2$ | $K_2O$ |
|---|---|---|---|---|---|
| Point 1 | 0.101 | 1.398 | 3.567 | 5.397 | 0.061 |
| Total amount | CaO | $TiO_2$ | $Cr_2O_3$ | MnO | FeO |
| 13.801 | 0.028 | 0 | 0 | 0.079 | 3.17 |
| Point 2 | 4.675 | 1.398 | 13.999 | 5.397 | 0.061 |
| Total amount | CaO | $TiO_2$ | $Cr_2O_3$ | MnO | FeO |
| 66.4 | 0.028 | 0 | 0 | 0.079 | 3.17 |

In terms of the dotting position, point 1 is close to the outer layer of the chlorite coating, and point 2 is close to the inner layer of the chlorite coating. It is seen from the overall composition of chlorite electron probe that the contents of $SiO_2$, MgO, FeO and $Al_2O_3$ at the two dotting positions are relatively high, and the chlorite coating in the study area is consistent with the characteristics of being rich in iron and magnesium as described by previous researchers. It is seen from comparing the chemical component contents of point 1 and point 2 that the contents of $K_2O$ and $Na_2O$ in the inner chlorite coating are much higher than those in the outer chlorite coating, indicating that a large amount of potassium- and sodium-rich feldspar minerals may exist at the beginning of the growth process of the chlorite coating that transforms and forms the inner crystal; in addition, in the second stage of the chlorite coating growth process, a large amount of $Na^+$ generated by the transformation of early clay minerals to form inner crystal may also cause an increase in the content of $Na_2O$. The proportion of MgO and FeO in the inner crystal is smaller than that in the outer crystal, which is consistent with the transfer of iron and magnesium ions during the transformation of the inner crystal to form the outer chlorite. In addition, the rich intermediate-basic rock debris, dark minerals (Table 1, FIG. 4) and adjacent mudstones observed in the thin sections make the pore water rich in $Fe^{2+}$ and $Mg^{2+}$, which can provide a material source for the growth of the outer chlorite coating.

S2: Performing Data Preprocessing on the Sample.

The chlorite has a general structural formula of $(R^{2+}, R^{3+})_{5-6}[(Si,Al_4O_{10})](OH)_8$. According to the results of whole-rock clay mineral X-diffraction experimental analysis, the main components of rock sample developed with chlorite are quartz, feldspar (potassium feldspar and plagioclase), laumontite and calcite. The quartz is mainly composed of silicon dioxide, laumontite is an aluminosilicate mineral, and calcite is a carbonate mineral. The main components of feldspar are silicates, the most common of which are potas-sium feldspar, albite, anorthite and celsian, which are rich in $K^+$, $Na^+$, and $Ca^{2+}$ respectively, the potassium feldspar is more common, the common species of albite and anorthite are sodium-rich and calcium-rich subspecies of plagioclase; and the main component of dolomite is calcium carbonate ($CaCO_3$). According to the results of X-ray diffraction experiments on clay minerals, the main minerals coexisting with chlorite are illite and kaolinite, with a small amount of illite/smectite mixed layer, all of which are aluminosilicate minerals. The mixed layer is mainly composed of illite and contains a small amount of smectite. Current study has shown that illite can be transformed into kaolinite and then into chlorite, and smectite and kaolinite can also be directly transformed into chlorite under certain conditions. The transformation equation is as follows:

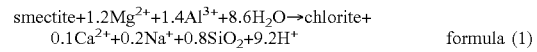

$$\text{smectite} + 1.2Mg^{2+} + 1.4Al^{3+} + 8.6H_2O \rightarrow \text{chlorite} + 0.1Ca^{2+} + 0.2Na^+ + 0.8SiO_2 + 9.2H^+ \quad \text{formula (1)}$$

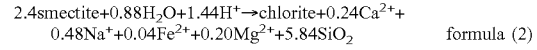

$$2.4\text{smectite} + 0.88H_2O + 1.44H^+ \rightarrow \text{chlorite} + 0.24Ca^{2+} + 0.48Na^+ + 0.04Fe^{2+} + 0.20Mg^{2+} + 5.84SiO_2 \quad \text{formula (2)}$$

In the formula (1), due to the participation of Al3+, Mg2+ enters montmorillonite to be subjected to replacement reaction to form an illite/smectite mixed layer and finally transformed into chlorite; the formula 2 is the process in which smectite is first dissolved and then precipitated, and is then replaced by chlorite; and under certain conditions, illite can be first transformed into kaolinite and then transformed into chlorite (formula 3).

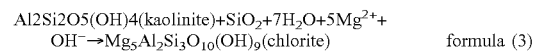

$$Al2Si2O5(OH)4(\text{kaolinite}) + SiO_2 + 7H_2O + 5Mg^{2+} + OH^- \rightarrow Mg_5Al_2Si_3O_{10}(OH)_9(\text{chlorite}) \quad \text{formula (3)}$$

By referring to the knowledge related to the combination of chemical compositions of various minerals and the growth process of chlorite and combining the above experimental contents, the initial set values of various minerals in the initial growth environment of chlorite are selected and the range is limited. First, the range of the proportion of mineral types is limited: for feldspar minerals, the content of $K_2O$ and $Na_2O$ in the inner crystal is close to 10%, while the relative content of which in the outer crystal is only about 1%, which indicates that a large number of feldspar minerals may be involved in the growth process of the inner chlorite crystal, and initial composition parameters of the eldspar minerals participating in the growth process of chlorite crystal exceed 10%. Although the types of minerals continue to change during the sedimentation and diagenesis process, the mass of elements is constant according to the law of conservation of matter. Therefore, according to the results of whole-rock clay mineral analysis, feldspar accounts for 28.8%. Excluding the possibility that uneven sample distribution and experimental errors may cause changes in distribution characteristics at different depths, the upper limit of the range of the feldspar proportion parameters in the initial environment should be set at more than 28.8%. For the remaining minerals, the preliminary setting ranges of relevant parameters are obtained according to similar steps based on the corresponding generation and consumption effects in the sedimentation process: the upper limit of the quartz setting is over 39%; the calcite setting value is less than 17.9%, and the lower limit of the calcite setting is about 0.3%; the upper limit of the dolomite setting value is about 1%; the laumontite setting value is less than 37%; the montmorillonite setting value is greater than 1.75%; the upper limit of the illite setting value is about 4%; and the upper limit of the kaolinite setting value is close to 2.4%. In addition, the smectite is a transformation product between clay minerals, and the value of the smectite is not considered in the initial environmental parameter setting; chlorite, laumontite, montmorillonite, illite, kaolinite, and the like are aluminosilicate minerals, and the upper limit of the sum of the relative contents of these minerals refers to the $Al_2O_3$ content ratio in the electron probe experiment results, and the upper limit of the sum of the set values is about 21%. In addition to the mineral types measured in the above experiments, there are a certain number of rich intermediate-basic igneous rock debris and ferromagnesian dark minerals near the study area that are transported to the study area and participate in the growth process of chlorite after a series of chemical reactions. The proportion of such rock debris to dark minerals is set at a reference range of greater than 1%, referring to the microscopic identification report of the rock thin section of the study area (Table 1). On this basis, the mineral types are refined according to the geological characteristics of the study area: referring to the microscopic characteristics (FIG. 4) and observation reports (Table 1) of the thin section, combined with the rock debris data in the relevant literature of the study area, the mineral types that may participate in the growth process of chlorite under actual geological conditions are supplemented: dawsonite, pyrite, and siderite. Considering that the favorable growth environment of chlorite is the material basis for iron-magnesium ions, combined with experimental test data, ankerite mineral is added. The mineral types finally determined are quartz, calcite, dolomite, ankerite, albite, potassium feldspar, oligoclase, kaolinite, illite, laumontite, chlorite, calcium montmorillonite, sodium montmorillonite, dawsonite, pyrite, siderite, and the like.

The continental lake basin in the study area has developed sedimentary strata dominated by a sand-mud interbedded layer. The observed chlorite mineral is developed in sandstone sample. According to oil field drilling data, the sandstone layer where the chlorite sample is positioned has a thickness of about 50 m, the underlying mudstone layer has a thickness of about 20 m, and the overlying mudstone layer has a thickness of about 30 m. There are abundant literature reports on the paleotemperature and paleosalinity of the strata in the study area. With reference to the data results, the initial salinity of the simulation experiment is set to 16.2‰ in combination with the simulation program. According to the relevant formula:

$$s \text{ (salinity ‰)} = \omega(\text{salt mass fraction \%})/10 \qquad \text{formula (4)}$$

The salt mass fraction in the study area is calculated to be 0.0162, the initial temperature is set at 25° C. with reference to the temperature data, and the experimental reaction temperature is set to 40° C. with reference to the predicted temperature of 40° C. to 50° C. for chloritization of early clay precursors (Hillier and Velde, 1991; Beaufort et al., 2015; Azzam et al., 2022).

S3: Establishing a Water-Rock Numerical Simulation Model.

Tough-2 is a numerical simulation program for multiphase fluids and heat transfer in porous/fractured media, and Tough-react is a numerical simulation program for non-isothermal flow chemical reactions in multiphase fluids, including reactions between mineral aggregates and liquids under local equilibrium or dynamic rate conditions. The composition and environment of paleofluids are important factors in numerical simulation. The Fe—Mg—Al—Si—O—NaOH system and $(Fe, Mg, Al)(OH)n\text{-}SiO_2\text{-}H_2O$ thermodynamic system are mainly used to simulate the precipitation process. The EWASG state equation (fluid properties: water, NaOH, $O_2$) is mainly used in the water-rock numerical simulation model. The relevant equations involved in the growth of chlorite are set with reference to formula 1, formula 2, and formula 3. Based on Darcy's law and molar conservation constant, the simulation experiment process is combined with water-rock numerical simulation to solve the seepage characteristics under multiphase fluid conditions by using formula 5 and formula 6.

$$u_\beta = -kk_{r\beta}(\delta_{p\beta} - \rho_\beta g)/\mu_\beta \qquad \text{formula (5)}$$

$$p_\beta = p + p_{c\beta} \qquad \text{formula (6)}$$

wherein u represents a seepage velocity vector; k represents total permeability in mD; μ represents a viscosity; p represents a pressure in Pa; ρ represents a liquid density in kg/m³; g represents a gravity vector in N/kg; β represents different phases; $k_{r\beta}$ represents a relative permeability of a corresponding phase (values between 0 and 1) in mD; $p_\beta$ represents a fluid pressure in a corresponding phase in Pa; and $p_{c\beta}$ represents a capillary pressure in Pa.

A basic mass and energy balance equation in the water-rock interaction numerical simulation can usually be expressed as:

$$\frac{d}{dt}\int_{V_n} M^k dv_n = \int_{T_n} F^k * n\, dT_n + \int_{V_n} q^k dv_n \qquad \text{formula (7)}$$

wherein $V_n$ is a subarea with a grid of n, $v_n \in V$, and v represents a study area; $T_n$ is an enclosed area in m²; M represents mass or energy per unit volume in kg or J/m³; F is mass or heat flux in kg or J; and q represents sink and source of a fluid.

During the numerical simulation, the model is spatially discretized using continuity equations according to the integral finite difference method. The average volume can then be calculated by using formula 8.

$$\int_{v_n} M \, dV = v_n M_n \qquad \text{formula (8)}$$

wherein M is volume normalized; and $M_n$ is a dimensionless average of M over $v_n$.

$$\int_{T_n} F^k \cdot n dT_n = \sum_m A_{nm} F_{nm} \qquad \text{(formula 9)}$$

wherein $F_{nm}$ is the average of the normal components of the surface portions F (inward) of $v_n$ and $A_{nm}$.

An average value of element parameters is used to represent a discrete flux, and $v_n$ fits a basic Darcy flux term. Then, formula 10 is used:

$$F_{\beta nm} = -k_{nm} \left[\frac{k_{r\beta}\rho_\beta}{\mu_\beta}\right]_{nm} - \left[\frac{p_{\beta,n} - p_{\beta,m}}{Dnm} - \rho_{\beta,nm} g_{nm}\right] \qquad \text{formula (10)}$$

wherein the subscript (nm) represents the appropriate average (interpolation, harmonic weighting, and upstream weighting) at the section between grid n and grid m; Dnm=Dn+Dm represents a distance between grid n and grid m; and $g_{nm}$ refers to the component of gravitational acceleration from m to n.

By substituting the average volume and surface integral into the mass and energy balances, a set of first-order ordinary differential equations is obtained.

$$\frac{dM_n^k}{dt} = \frac{1}{v_n} \sum_m A_{nm}^k F_{nm}^k + q_n^k \qquad \text{formula (11)}$$

The time is discretized into first-order finite differences, and the fluxes, sinks, and sources on the right are evaluated at the new times to obtain the numerical stability required for efficient computation of multiphase flows.

Figure 6:
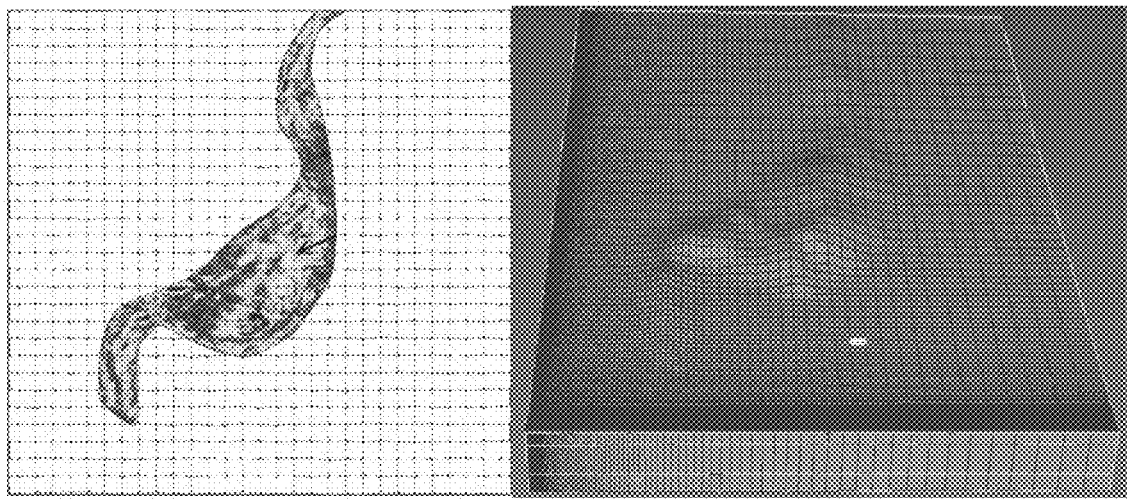
FIG. 6 is a schematic diagram of a three-dimensional model construction of a water-rock numerical simulation experiment according to an embodiment of the present invention.

S4: Developing a Water-Rock Numerical Simulation Experiment;

Guided by the planar distribution characteristics of the delta front in the study area, the three-dimensional geodetic coordinates of the target work area are obtained by combining the three-dimensional digital extraction software Getdata. On the basis of clarifying the layering characteristics of the target layer and the upper and lower layers in the key well area, a stratigraphic framework model consistent with the proportions of the study area is established, mudstone-sandstone-mudstone is sequentially arranged from bottom to top, and the rock layer thickness is consistent with the actual well area as much as possible. The simulation thickness is set to 20 m, 50 m and 30 m respectively with reference to the actual geological conditions. The discrete network construction technology of the combined water-rock numerical simulation software is used to construct a three-dimensional grid model of the target layer in the study area by setting the grid scale factor in the x-axis and y-axis directions to 1.0495 and the grid in the z-axis direction based on the layering standard (FIG. 6). Combined with the geochemical test results of chlorite sample and the oilfield production test results, the initial model parameters of water-rock simulation are determined, including relevant parameters of sandstone and mudstone layers such as density, porosity, permeability in three directions, hygroscopic thermal conductivity, specific heat and calculation method of relative permeability. The chemical parameters corresponding to sandstone and mudstone are shown in Table 5.

During the simulation, the actual conditions of the chlorite growth process and the reaction process of each fluid are considered, and the initial temperature is set to 25° C., the reaction temperature is 40° C., the initial pressure is 2.0 e7 Pa, and the salt mass fraction is 0.016. With reference to the actual growth environment of chlorite in the study area, the EWASG state response model is selected as the model in the water-rock numerical simulation program. Based on the chlorite mineral analysis results obtained by in-situ high-precision observation in steps I and II, combined with the actual principles of the simulation program, and based on the test results in the study area, the initial chemical reaction ions are set to $AlO^{2-}$, $Fe^{2+}$, $Fe^{3+}$, $H_2O$, $K^+$, $Mg^{2+}$, $Na^+$, $O_2(aq)$, and $OH^-$. The chemical ion components involved in the water-rock numerical simulation process include: $Al(OH)^{2+}$, $Al(OH)_3(aq)$, $Al^{3+}$, $AlOH^{2+}$, $Fe^{3+}$, $FeCl^+$, $FeCl_4^{2-}$, $HAlO_2(aq)$, $SiO_3^{2-}$, $KCl(aq)$, $MgCl^+$, $MgSO_4(aq)$, $NaAlO^2(aq)$, $NaCl(aq)$, and $NaOH(aq)$. The above ions can meet the necessary ions and environmental conditions required by the water-rock numerical program to simulate the growth of chlorite mineral, which provides a reliable guarantee for simulating the patterns and influencing factors of the chlorite growth process.

On the basis of determining the initial ions in the water-rock simulation experiment and the mineral ions involved in the reaction in the solution, the mineral types and proportions in the chlorite growth simulation model are set according to the mineral types extracted in the previous descriptions, and then all parameters including the grain radius (m), surface area (m²) and unit of each mineral are improved in combination with the numerical simulation program. The mineral types include albite, dawsonite, potassium feldspar, oligoclase, magnetite, quartz, chlorite, and the like. The specific parameter settings are shown in Table 6.

TABLE 5

Chemical parameters of sandstone and mudstone in water-rock numerical simulation.

| Type | Density (kg/m³) | Porosity | X-direction permeability (m²) | Y-direction permeability (m²) | A-direction permeability (m²) | Hygroscopic thermal conductivity (W/(m * K)) | Specific heat capacity (J/(kg * K)) |
|---|---|---|---|---|---|---|---|
| Sandstone | 2600 | 0.3 | 1.0e−12 | 1.0e−12 | 1.0e−12 | 2.51 | 460 |
| Mudstone | 2350 | 0.2 | 1.0e−13 | 1.0e−13 | 1.0e−13 | 1.15 | 460 |

The radius of mineral grains is set to 0.001 m, and the unit is cm²/g mineral. The proportions of minerals such as albite are set to 0.015, 0.004, 0.00497, 0.08179, 0.19795, 0.001, 0.57888, and 0.004556. Similarly, the surface area sizes of minerals such as albite are set to 9.8, 9.8, 9.8, 9.8, 9.8, 151.63, 9.8, 151.6, 9.8, 12.87, 9.8, 9.8, 151.63, 151.63, 9.8, and 9.8. All parameter settings refer to the values of different mineral chemical parameters in the numerical simulation software PetraSim. After setting the chemical composition and mineral parameters, the fluid inlet and fluid injection method of the study area are defined. During this study, three substances of water, NaOH and $O_2$ are injected. The injection flow rates and enthalpy of three substances are 30 kg/s and 920.0 J/kg, 15 kg/s and 920.0 J/kg, and 10 kg/s and 920.0 J/kg, respectively. Then, the relevant steps of the simulation process, such as the start time, the end time, and maximum time step of the water-rock numerical simulation, are set for the chlorite growth simulation experiment.

TABLE 6

Chemical minerals and composition characteristics in the water-rock interaction simulation model

| Mineral | Proportion | Grai radius (m) | Surface area (m²) | Unit |
|---|---|---|---|---|
| Albite | 0.015 | 0.001 | 9.8 | cm²/g mineral |
| Ankerite | 0.005 | 0.001 | 9.8 | cm²/g mineral |
| Calcite | 0.01929 | 0.001 | 9.8 | cm²/g mineral |
| Dawsonite | 0.004 | 0.001 | 9.8 | cm²/g mineral |
| Dolomite | 0.001 | 0.001 | 9.8 | cm²/g mineral |
| Illite | 0.00954 | 0.001 | 151.63 | cm²/g mineral |
| Potassium feldspar | 0.08179 | 0.001 | 9.8 | cm²/g mineral |
| Kaolinite | 0.02015 | 0.001 | 151.6 | cm²/g mineral |
| Oligoclase | 0.19795 | 0.001 | 9.8 | cm²/g mineral |
| Pyrite | 0.005 | 0.001 | 12.87 | cm²/g mineral |
| Quartz | 0.57888 | 0.001 | 9.8 | cm²/g mineral |
| Siderite | 0.0066 | 0.001 | 9.8 | cm²/g mineral |
| Calcium montmorillonite | 0.0028 | 0.001 | 151.63 | cm²/g mineral |
| Sodium montmorillonite | 0.03897 | 0.001 | 151.63 | cm²/g mineral |
| Chlorite | 0.004556 | 0.001 | 9.8 | cm²/g mineral |
| Laumontite | 0.0065 | 0.001 | 9.8 | cm²/g mineral |

S5: Analyzing a Water-Rock Numerical Simulation Result.

Based on the water-rock numerical simulation software platform PetraSim and combined with the above experimental principles and experimental steps, the distribution state of chlorite during the growth simulation experiment and the final distribution state after the simulation experiment are intercepted, and the distribution characteristics of chlorite mineral in the target layer of the study area are studied.

To analyze the distribution characteristics of chlorite in detail, three north-south measuring lines and three east-west measuring lines are selected based on the chlorite distribution diagram after the simulation experiment to obtain the distribution characteristics of chlorite content on the longitudinal section. According to the simulation results, blue represents areas with relatively low chlorite content, cyan represents areas with a certain chlorite content, and red and yellow represent areas with higher chlorite content.

Analysis is performed by combining actual geological conditions:

In the work area, the fluid flows from north to south, and the fluid dynamics becomes slightly lower; and then the fluid passes through the narrow area and enters the open area, where the deposition range expands and the fluid kinetic energy increases. Then the terrain changes again, and the fluid deposition range shrinks again. From north to south, the fluid dynamics are first strong, then weak, and then strong again, and finally decrease until deposition ends. From east to west, the middle part has the strongest sedimentation dynamics, and the fluid dynamics gradually weaken towards the sides.

Figure 7:
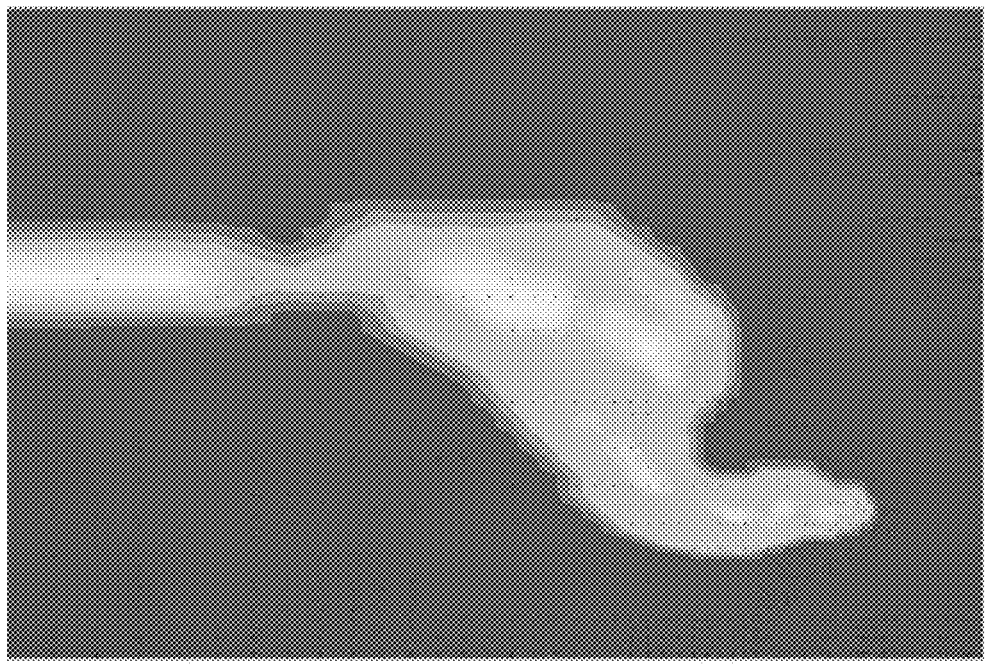
FIG. 7 shows a planar distribution characteristic of a chlorite growth simulation experiment according to an embodiment of the present invention.

In the process diagram (FIG. 7), the overall color is slightly cyan, which indicates that the overall chlorite content is not high, but the middle part of the sediment shows a yellow indicator color, which means that the chlorite content is enriched in these areas. Along the flow direction, the chlorite distribution concentration is the highest at the fluid outlet, and the chlorite enrichment decreases with the increase of fluid flow distance. In the tangential direction of the flow, chlorite growth is concentrated in the middle of the model where the hydrodynamics is stronger. In the final chlorite distribution diagram (FIG. 8), the overall color is blue, which indicates a low content. The chlorite content outside the enriched area in the process diagram (FIG. 7) is significantly lower; the indicator color of the enriched area is overall yellow, and some areas can be red, which is significantly higher than the chlorite content in the process diagram (FIG. 7). A detailed analysis is performed on the different measuring directions selected in the final distribution diagram (FIG. 8): In the downstream direction, A-A' has a thin layer of sediment at the end of the fluid, corresponding to weak hydrodynamics, and the chlorite content formed is relatively low; B-B' cuts through the section with enhanced water kinetic energy, and it can be seen that the sediment thickness has increased significantly, and a yellow indicator color with significant thickness appears in the middle, indicating an increase in the relative content of chlorite mineral; and C-C' section is at the edge where the fluid kinetic energy is weak, and the thickness is significantly thinner and the indicator color is blue. In the east-west direction, F-F' crosses the fluid, the sediments are more concentrated and thicker, the relative content of chlorite is significantly higher, and a red indicator color appears, and the yellow area indicates that the distribution of chlorite is significantly wider and more concentrated; E'-E is also in the middle of the fluid, crosses a wider range of the fluid, and the sediments are wider and thicker, but the indicator color shows that the chlorite growth range is not as concentrated as that of F-F'; and at the far end D-D', the fluid width is greatly reduced, and chlorite is only slightly concentrated in the middle of the sediment. It can be seen from comparing the chlorite growth process diagram with the final distribution diagram that, in the final distribution diagram, the chlorite enrichment degree is higher and the range is wider, and the red and yellow indicator colors are more obvious; and the indicator color of the area far away from the enrichment point is darker than that of the process diagram, indicating a decrease in the chlorite content outside the enrichment point. In summary, the results of the chlorite growth simulation experiment are roughly consistent with the enrichment trend shown in the chlorite growth process, which both indicate that chlorite is enriched and grows in the middle of the sediment with strong hydrodynamics.

S6: Explaining and Applying the Water-Rock Numerical Simulation Result.

According to the results of water-rock numerical simulation analysis, the growth and enrichment pattern of chlorite in the work area is correlated with the strength of hydrodynamics.

In the process diagram (FIG. 7), a certain amount of chlorite is generally developed in the areas outside the enrichment point, which may be because the fine-grained clay including chlorite in the solution is adsorbed on the surface of the grains to form a clay ring. In an environment with strong hydrodynamics, primary intergranular pores are developed between sediment grains, there is relatively more clay adsorbed on the surface of the grains, and the iron-rich clay mineral coating formed by the hydrolysis and recrystallization of iron flocs under the difference in salinity between the injected solution and the formation model is enriched in the primary intergranular pores. Therefore, chlorite is significantly enriched in the middle of the sediment with strong hydrodynamics.

In the final distribution diagram of the chlorite growth model (FIG. 8), the enrichment pattern is similar to that in the process diagram (FIG. 7). The chlorite is most enriched at the solution injection port. This is because the iron flocs under the salinity difference are the most abundant at the solution intersection, which can provide a large amount of iron and magnesium ions required for the growth of chlorite. It can also be inferred that a large amount of iron flocs are the main source of material for the growth of chlorite in the study area. Therefore, the chlorite content at the injection port is much higher than that in other enriched areas. There are also certain differences between the process diagram and the final distribution diagram: the chlorite content in the area outside the enrichment point in the final distribution diagram becomes significantly lower, and chlorite content in this area is more enriched in the enriched area, and gradually decreases from the center to the periphery, which indicates that chlorite has undergone transformation or migration in the later stage of the simulation experiment. Combined with the experimental conditions, the generated clay minerals are transformed into chlorite from the pore water rich in iron and magnesium ions in an alkaline environment. In addition, chlorite can also be directly generated in the pore water rich in iron and magnesium ions in the later stage. The development of primary intergranular pores is conducive to the movement of pore fluids and thus to more complete ion exchange. In the late stage of early clay film transformation reaction, the flow of pore fluids may move favorable ions outside the enrichment area into the primary pores to participate in the formation of chlorite, resulting in chlorite enrichment in the area with developed primary pores. Although chlorite is generated outside the area, the consumption and migration of chlorite reduces the chlorite content. Therefore, in the final distribution diagram, chlorite is increasingly enriched in the environment with stronger hydrodynamics.

According to the results of the chlorite growth simulation experiment, in the medium and low temperature (70° C.) environment of clastic sandstone, the chlorite growth order is as follows: the early clay coating containing chlorite is widely developed in the solution—the clay coating is transformed into granular film chlorite (inner crystal of chlorite coating)—pore lining chlorite (outer crystal of chlorite coating) generated in pore water and enriched in primary pores, among which the chlorite in the early clay coating has a relatively wide distribution range but a low content, and the granular film chlorite and pore lining chlorite generated later have relatively high contents, and the chlorite is easier to grow closer to the intersection of the deposition medium. In addition, factors that affect the growth of chlorite include salinity, iron and magnesium ion content, acidity and alkalinity, and the like. A certain difference in salinity, a higher iron and magnesium ion content, and an alkaline environment can provide sufficient material sources for the formation of chlorite, which is more conducive to the formation of chlorite. Based on the comprehensive experimental results, in the environment where rivers enter lakes (salinization) and under the condition that iron flocs provide the main source of material, the growth of chlorite is mainly controlled by sedimentation, the chlorite is enriched in an environment with strong hydrodynamics, and the closer to the lake (sea) entrance, the higher the enrichment degree. This pattern can provide a reference for the study of the growth pattern of chlorite in low-temperature sandstone in other basins.

The above descriptions are only preferred embodiments of the present invention. It should be noted that those of ordinary skill in the art can also make several improvements and modifications without departing from the principle of the present invention, and such improvements and modifications shall fall within the protection scope of the present invention. The structures, devices and operating methods not specifically described and explained in the present invention shall be implemented according to conventional means in the art unless otherwise specified and limited.

What is claimed is:

1. A study method for chlorite growth pattern based on an in-situ high-precision observation means, comprising the following steps:
    S1: selecting a sample and quantitatively characterizing mineral components; wherein the S1 comprises the following substeps:
    S11: selecting a typical sandstone sample developed with a chlorite coating and cement, grinding a rock slice, and observing under a microscope and a scanning electron microscope to determine a basic morphological characteristic, occurrence state and type of the chlorite;
    S12: performing a whole-rock clay mineral X-ray diffraction experiment on the same sandstone sample to obtain types and contents of related minerals contained in a chlorite growth environment;
    S13: selecting a proper observation point to perform electron probe and energy spectrum analysis experiments on a chlorite developed with a typical grain coating, a pore lining and a pore filling in the sample based on a growth sequence from early to late to obtain element types and mineral component contents of different types of chlorites;
    S2: performing data preprocessing on the sample; wherein the data preprocessing in the S2 is performed in the following manner:
    preliminarily extracting environmental conditions required by chlorite growth in different occurrences and growth stages from observation data and experimental results;
    preliminarily calculating types and contents of minerals required for chlorite growth at different stages, reactive ions involved in the growth process, and a range of formation temperature and pressure parameters, so as to provide actual geological data support for water-rock numerical simulation;
    S3: establishing a water-rock numerical simulation model; wherein in the S3, combined with results of geochemical test analysis, a chlorite growth environment in an actual sample is determined, environmental conditions and fluid characteristic parameters required by chlorite growth are supplemented and improved, a simulation equation suitable for the chlorite sample is selected, and a chlorite water-rock interaction numerical model conforming to geological conditions of a study area is established;
    a seepage characteristic is solved under multiphase fluid conditions:

$$u_\beta = -kk_{r\beta}(\delta p_\beta - \rho_\beta g)/\mu_\beta$$

$$p_\beta = p + p_{c\beta}$$

wherein u represents a seepage velocity vector; k represents total permeability in mD; μ represents a viscosity; p represents a pressure in Pa; ρ represents a liquid density in kg/m³; g represents a gravity vector in N/kg; β represents different phases; $k_{r\beta}$ represents a relative permeability of a corresponding phase in mD; $p_\beta$ represents a fluid pressure in a corresponding phase in Pa; and $p_{c\beta}$ represents a capillary pressure in Pa;

a basic mass and energy balance equation in the water-rock interaction numerical simulation can usually be expressed as:

$$\frac{d}{dt}\int_{v_n} M^k dv_n = \int_{T_n} F^k * n\, dT_n + \int_{v_n} q^k dv_n$$

wherein $v_n$ is a subarea with a grid of n, $v_n \in V$, and v represents a study area; $T_n$ is an enclosed area in m²; M represents mass or energy per unit volume in kg or J/m³, F is mass or heat flux in kg or J; and q represents the sink and source of a fluid;

during the numerical simulation, the model is spatially discretized using continuity equations according to an integral finite difference method, and an average volume is obtained by the following formula:

$$\int_{v_n} M\, dv = v_n M_n$$

wherein M is volume normalized; and $M_n$ is a dimensionless average of M over $v_n$:

$$\int_{T_n} F^k \cdot n dT_n = \sum_m A_{nm} F_{nm}$$

wherein Fnm is an average of normal components of surface portions F of $v_n$ and $A_{nm}$;

an average value of element parameters is used to represent a discrete flux, and $v_n$ fits a basic Darcy flux term;

$$F_{\beta nm} = -k_{nm}\left[\frac{k_{r\beta}\rho_\beta}{\mu_\beta}\right]_{nm} - \left[\frac{p_{\beta,n} - p_{\beta,m}}{Dnm} - \rho_{\beta,nm}g_{nm}\right]$$

wherein subscript nm represents an average at a section between grid n and grid m; Dnm=Dn+Dm represents a distance between grid n and grid m; and $g_{nm}$ refers to a component of gravitational acceleration from m to n;

by substituting the average volume and surface integral into the mass and energy balance equation, a set of first-order ordinary differential equations is obtained:

$$\frac{dM_n^k}{dt} = \frac{1}{v_n}\sum_m A_{nm}^k F_{nm}^k + q_n^k$$

the time is discretized into first-order finite differences, and fluxes, sinks, and sources on the right are evaluated at the new times to obtain a numerical stability required for efficient computation of multiphase flows;

S4: developing a water-rock numerical simulation experiment; wherein in the S4, according to the experimental parameter data obtained in the S2-S3, chlorite reaction models of different types and different growth stages are established based on water-rock numerical simulation modeling and reaction principles, and water-rock numerical simulation is performed;

S5: analyzing a water-rock numerical simulation result; wherein in the S5, the simulation result is obtained in the following manner: intercepting experiment charts under different time, temperature and pressure conditions based on the simulation experiment process and the growth time sequence of chlorite, and after performing analysis according to geological pattern to obtain growth models and distribution patterns of the chlorite at different development stages; and S6: explaining and applying the water-rock numerical simulation result; wherein in the S6, based on the analysis of the simulation experiment result, the simulation result is used to provide a reasonable and scientific geological and numerical model for the chlorite growth process in the sandstone, and to explain, optimize and predict the chlorite growth pattern.

2. The study method for chlorite growth pattern based on the in-situ high-precision observation means according to claim 1, wherein the environmental conditions required for chlorite growth comprise salinity, pH value, temperature, and pressure.

* * * * *